US011098156B2

(12) United States Patent
Sukumaran et al.

(10) Patent No.: US 11,098,156 B2
(45) Date of Patent: *Aug. 24, 2021

(54) METALLOPORPHYRIN 2D-SHEETS FOR EFFICIENT PHOTO- AND ELECTRO-CATALYTIC SPLITTING OF WATER

(71) Applicant: COUNCIL OF SCIENTIFIC & INDUSTRIAL RESEARCH, New Delhi (IN)

(72) Inventors: Santhosh Babu Sukumaran, Pune (IN); Ranjeesh Karayamkodath Chandran, Pune (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 47 days.

This patent is subject to a terminal disclaimer.

(21) Appl. No.: 16/465,918

(22) PCT Filed: Nov. 30, 2017

(86) PCT No.: PCT/IN2017/050560
§ 371 (c)(1),
(2) Date: May 31, 2019

(87) PCT Pub. No.: WO2018/100588
PCT Pub. Date: Jun. 7, 2018

(65) Prior Publication Data
US 2020/0071458 A1    Mar. 5, 2020

(30) Foreign Application Priority Data

Dec. 2, 2016  (IN) .............................. 201611041205

(51) Int. Cl.
*C07D 487/22*  (2006.01)
*C08G 61/12*  (2006.01)

(52) U.S. Cl.
CPC ......... *C08G 61/124* (2013.01); *C07D 487/22* (2013.01); *C08G 2261/124* (2013.01);
(Continued)

(58) Field of Classification Search
CPC .................................................... C07D 487/22
See application file for complete search history.

(56) References Cited

FOREIGN PATENT DOCUMENTS

WO    2018/100588 A1    6/2018

OTHER PUBLICATIONS

Ding et al., "An n-Channel Two-Dimensional Covalent Organic Framework," American Chemical Society, (2011) pp. 14510-14513.
(Continued)

*Primary Examiner* — Brian E McDowell
(74) *Attorney, Agent, or Firm* — Cantor Colburn LLP

(57) ABSTRACT

The present invention disclosed a novel squaraine linked metalloporphyrin based 2D sheet polymer catalyst of formula (I), process for preparation thereof and use of said catalyst for efficient photo- and electro-catalytic splitting of water.

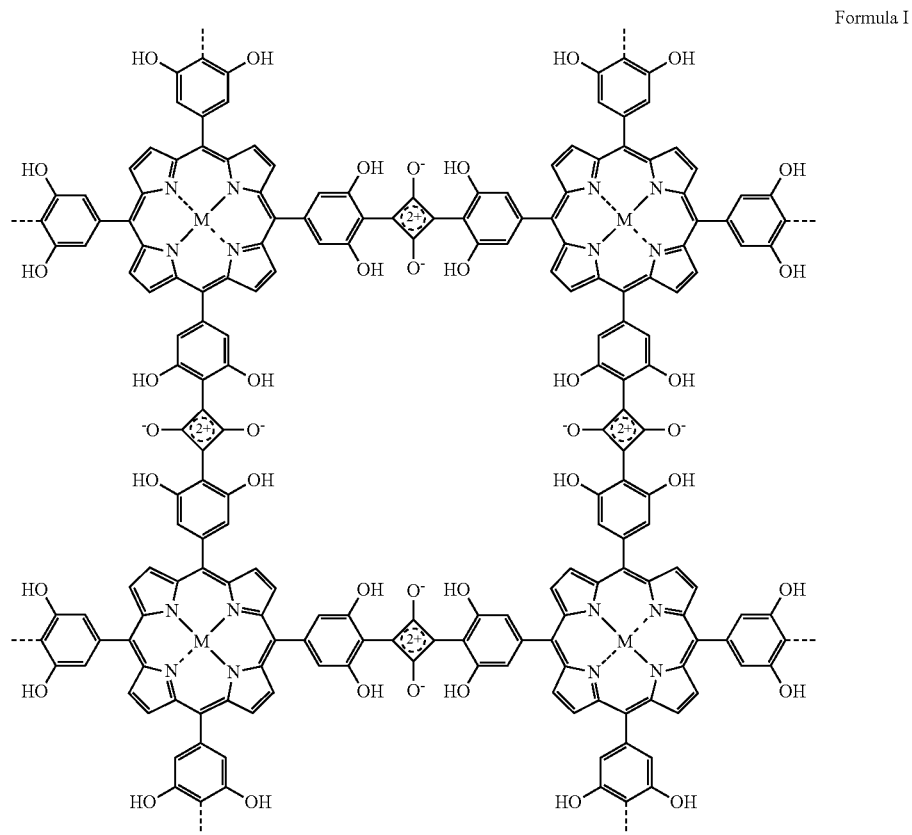

Formula I

10 Claims, 6 Drawing Sheets

(52) U.S. Cl.
CPC . *C08G 2261/132* (2013.01); *C08G 2261/312* (2013.01); *C08G 2261/3221* (2013.01); *C08G 2261/376* (2013.01)

(56) References Cited

OTHER PUBLICATIONS

Jia et al., "Pyrolyzed Cobalt Porphyrin-Based Conjugated Mesoporous Polymers as Bifunctional Catalysts for Hydrogen Production and Oxygen Evolution in Water" Chemical Communications, (2016) 52, pp. 13483-13486.

Neti et al., "Synthesis of a Phthalocyanine 2D Covalent Organic Framework," Cryst. Eng. Comm, (2013) 15, 7157-7160.

Ma et al., "An Efficient Electrocatalyst for Oxygen Reduction Reaction Derived from a Co-Porphyrin-Based Covalent Organic Framework," published in Electrochemistry Communications; Mar. 2015; 52, pp. 53-57.

Wang et al., "Two-Dimensional Porphyrin- and Phthalocyanine-Based Covalent Organic Frameworks," Chinese Chemical Letters, Aug. 2016, 27 (8), pp. 1376-1382.

You et al. "High-Performance Overall Water Splitting Electrocatalysts Derived from Cobalt-Based Metal-Organic Frameworks" Chem. Mater., (2015) 27(22), pp. 7636-7642.

Ashwell et al., "Aggregation-Induced Linear and Non-Linear Optical Properties of Four Hydroxy-Substituted Analogues of 2,[4-Bis[Dibutylaminio)phenyl]Squaraine," An Australian Journal of Chemistry, vol. 51, No. 7, Jul. 13, 1998; pp. 599-604.

International Search Report and Written Opinion for International Application No. PCT/IN2017/050560; International Filing Date—Nov. 30, 2017; dated Mar. 16, 2018; 11 pages.

Nagai et al., "A Squaraine-Linked Mesoporous Covalent Organic Framework," Angewandte Chemie International Edition, vol. 52, No. 13; Mar. 25, 2013, pp. 3770-3774.

Zhang et al., "Bottom-Up Approach to Engineer Two Covalent Porphyrinic Frameworks as Effective Catalysts for Selective Oxidation," Catalysis Science & Technology, vol. 5, No. 1, Sep. 24, 2015; pp. 101-104.

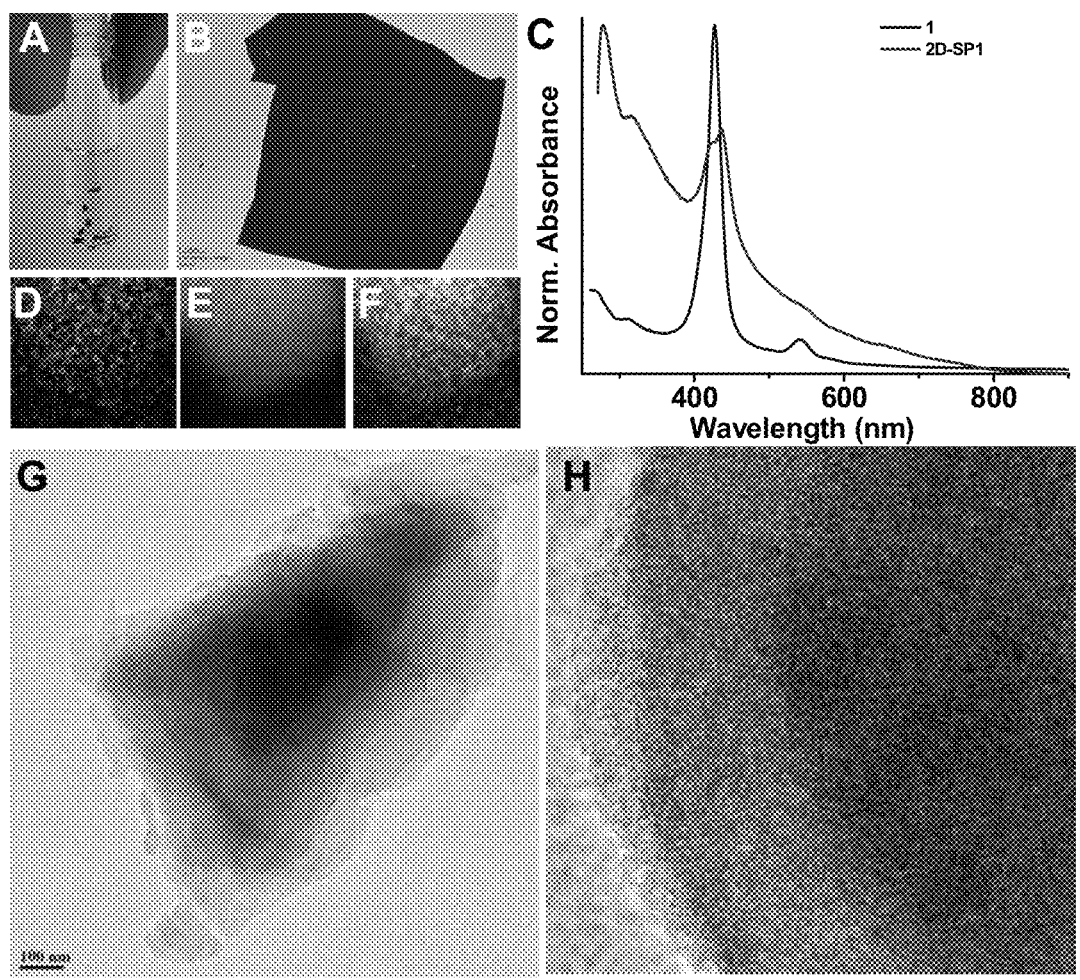
Fig: 1

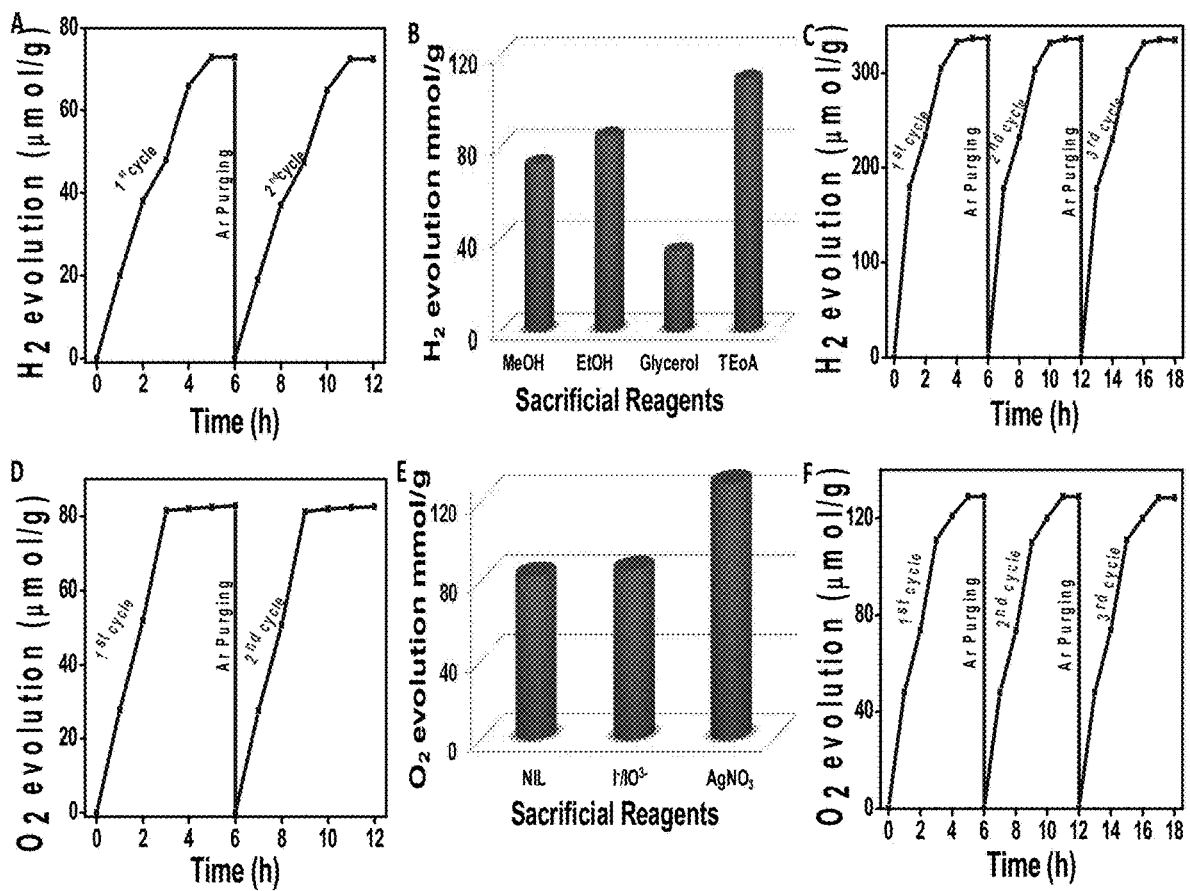
Fig: 2

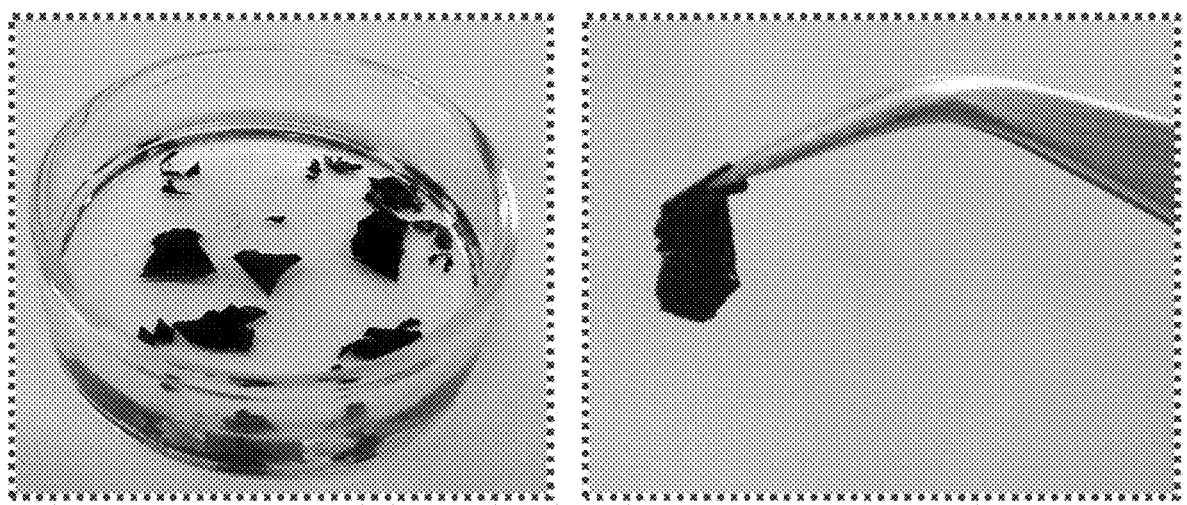
Fig: 3

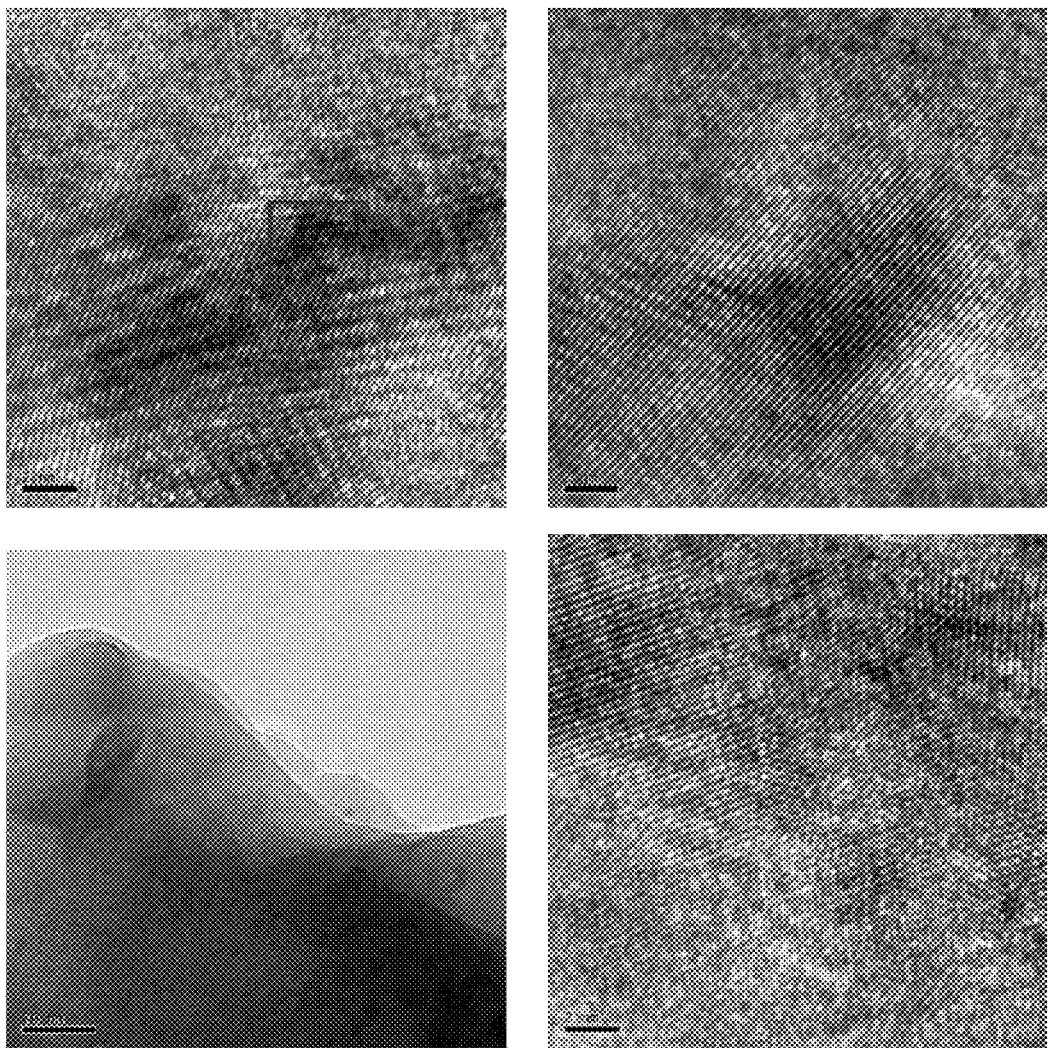
Fig: 4

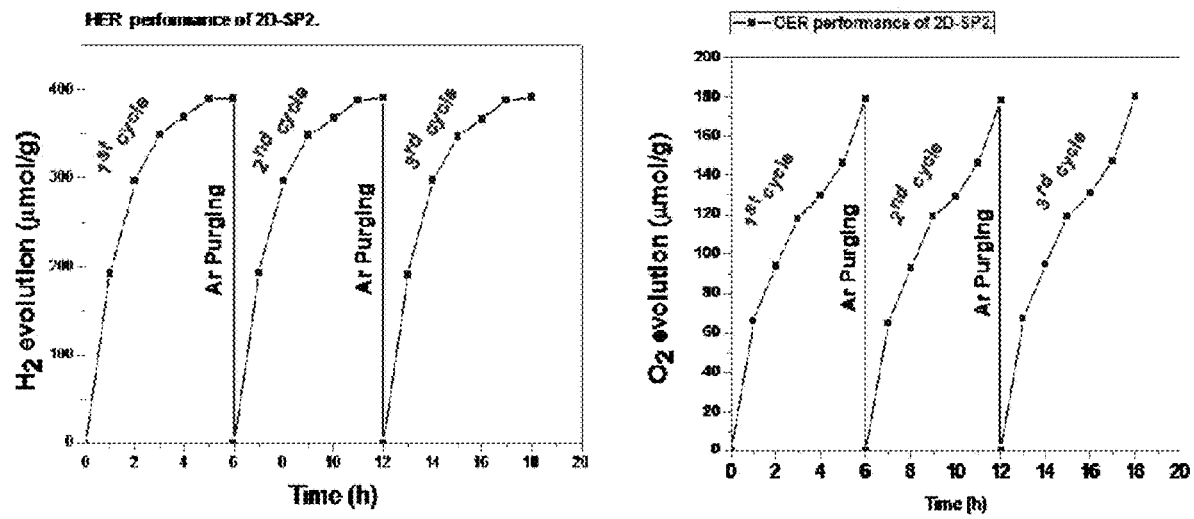
Fig: 5
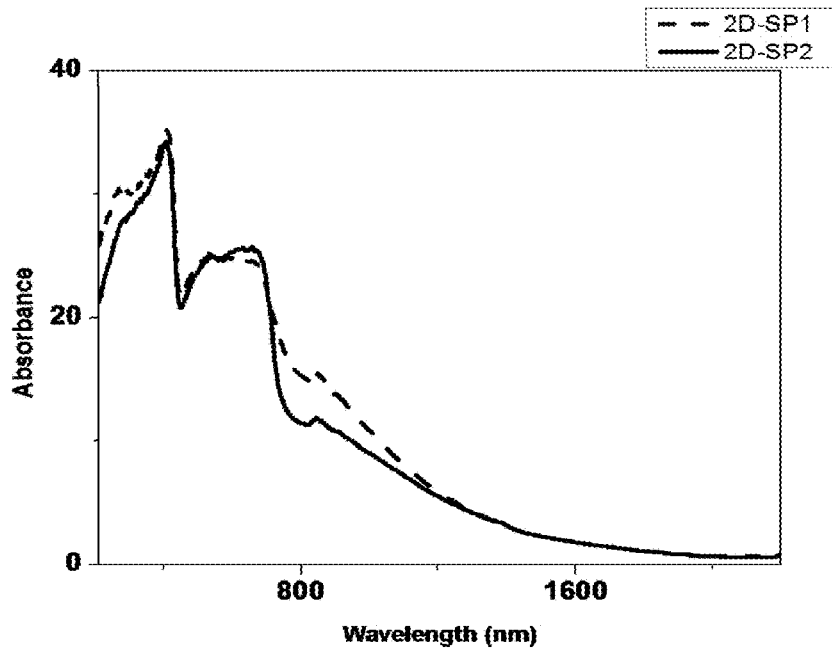
Fig: 6

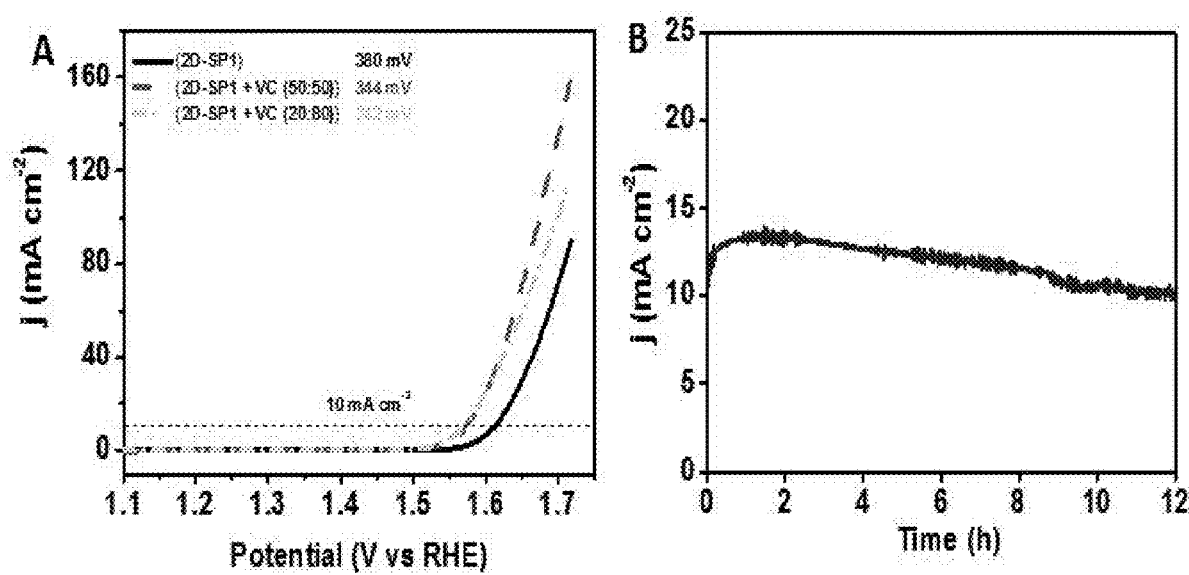
Fig: 7

METALLOPORPHYRIN 2D-SHEETS FOR EFFICIENT PHOTO- AND ELECTRO-CATALYTIC SPLITTING OF WATER

CROSS REFERENCE TO RELATED APPLICATIONS

This application is a National Stage application of PCT/IN2017/050560, filed Nov. 30, 2017, which claims priority to Indian Application No. 201611041205, filed Dec. 2, 2016, and all the benefits accruing therefrom under 35 U.S.C. § 119, the content of which is incorporated by reference in its entirety.

FIELD OF THE INVENTION

The present invention relates to a novel metalloporphyrin based 2D-sheet polymer catalyst. More particularly, the present invention relates to a novel squaraine linked metalloporphyrin based 2D-sheet polymer catalyst of formula (I), process for preparation thereof and use of said catalyst for efficient photo- and electro-catalytic splitting of water.

BACKGROUND AND PRIOR ART

Water splitting driven by sunlight or renewable resource-derived electricity has attracted great attention for sustainable production of hydrogen and oxygen from water. Current research interest in this field is focused on the development of earth-abundant photo- or electrocatalytic materials with high activity and long-term stability for hydrogen and/or oxygen evolution reactions. Water splitting reaction consists of two half reactions i.e. water reduction or $H_2$ evolution reaction (HER) and water oxidation or oxygen evolution reaction (OER). In the research on photocatalytic water splitting, these two reactions are mostly decoupled by employing sacrificial reagents due to enormous challenges in designing efficient photocatalysts for overall water splitting. In electrocatalytic water splitting, HER and OER occur at the cathode and anode separately, which allows for the design of optimal HER and OER catalysts individually.

The design of active, robust, and nonprecious electrocatalysts with both $H_2$ and $O_2$ evolution reaction (HER and OER) activities for overall water splitting is highly desirable but remains a major challenge. Further, to search for the efficient non-noble metal based and/or earth-abundant electrocatalysts for overall water-splitting is critical to promote the clean-energy technologies for hydrogen economy.

Article titled "A squaraine-linked mesoporous covalent organic framework" by A Nagai et al. published in *Angew Chem Int Ed Engl.*, 2013; 52 (13), pp 3770-3774 reports a squaraine-linked, conjugated two-dimensional porphyrin covalent organic framework by was synthesized. Owing to the π-conjugated linkage together with the eclipsed stacking of the units, this COF exhibits enhanced chemical and thermal stabilities. It absorbs a broad range of light, from the ultraviolet to the visible and near-infrared regions, and shows potential as a photocatalyst.

A review article titled "Two-dimensional porphyrin- and phthalocyanine-based covalent organic frameworks" by H Wang et al. published in *Chinese Chemical Letters*, August 2016, 27 (8), pp 1376-1382 reports two-dimensional (2D) porphyrin- and phthalocyanine-based COFs, with highlighting the synthesis of these 2D COFs via various dynamic covalent reactions and emphasizing their potential applications in different areas.

Article titled "An n-channel two-dimensional covalent organic framework" by X Ding et al. published in *J. Am. Chem. Soc.*, 2011, 133 (37), pp 14510-14513 reports Co-condensation of metallophthalocyanine with an electron-deficient benzothiadiazole (BTDA) block leads to the formation of a two-dimensional covalent organic framework (2D-NiPc-BTDA COF) that assumes a belt shape and consists of AA stacking of 2D polymer sheets.

Article titled "An efficient electrocatalyst for oxygen reduction reaction derived from a Co-porphyrin-based covalent organic framework" by W Ma et al. published in *Electrochemistry Communications*; March 2015; 52, pp 53-57 reports a novel efficient electrocatalyst for oxygen reduction reaction (ORR) synthesized by pyrolysis of a cobalt-based covalent organic framework, which shows electrocatalytic performance comparable with the commercial Pt/C for ORR via an almost four-electron pathway in alkaline media without methanol-crossover effect.

Article titled "Synthesis of a phthalocyanine 2D covalent organic framework" by VSPK Neti et al. published in *Cryst Eng Comm*, 2013, 15, 7157-7160 reports a new two-dimensional cobalt based phthalocyanine covalent organic framework (CoPc-BPDA COF) synthesized under solvothermal conditions.

Article titled "Pyrolyzed cobalt porphyrin-based conjugated mesoporous polymers as bifunctional catalysts for hydrogen production and oxygen evolution in water" by H Jia et al. published in *Chem. Commun.*, 2016, 52, 13483-13486 reports a series of cobalt porphyrin-based conjugated mesoporous polymers (CoP-nph-CMP, n=2, 3, 4) fabricated as catalyst precursors to generate bifunctional catalysts via pyrolysis (CoP-nph-CMP-800, n=2, 3, 4) for both the oxygen evolution reaction (OER) and the hydrogen evolution reaction (HER). Further, their excellent bifunctional catalytic performance was also explored in the overall water splitting test.

Article titled "High-Performance Overall Water Splitting Electrocatalysts Derived from Cobalt-Based Metal-Organic Frameworks" by B You et al. published in *Chem. Mater.*, 2015, 27 (22), pp 7636-7642 reports a facile two-step method to synthesize porous Co—P/NC nanopolyhedrons composed of $CoP_x$ (a mixture of CoP and $Co_2P$) nanoparticles embedded in N-doped carbon matrices as electrocatalysts for overall water splitting.

An efficient catalyst for splitting water to generate oxygen and hydrogen using solar energy is one of the demanding and cost effective method of renewable energy storage. However, even after several decades of research, a single durable material which work both as an effective photo and electro catalyst for water splitting has rarely been attempted.

Therefore, there is need to develop a catalyst for efficient photo- and electro-catalytic splitting of water. Accordingly, the inventors provide squaraine linked metalloporphyrin based 2D-sheet polymer catalyst for production of hydrogen and oxygen from water.

OBJECTIVE OF THE INVENTION

The main objective of the present invention is to provide a novel squaraine linked metalloporphyrin based 2D-sheet polymer catalyst of formula (I).

Another objective of the present invention is to provide a one step process for the synthesis of squaraine linked metalloporphyrin based 2D-sheet polymer catalyst of formula (I).

Yet another objective of the present invention is to provide a use of novel squaraine linked metalloporphyrin based 2D-sheet polymer catalyst of formula (I) for generation of oxygen and hydrogen by splitting water photo catalytically and electro catalytically.

SUMMARY OF THE INVENTION

Accordingly, the present invention provides a novel squaraine linked metalloporphyrin based 2D-sheet polymer catalyst with basic unit of formula (I);

wherein;
M is selected from cobalt, nickel, zinc, copper, iron, manganese, molybdenum or mixture thereof.

In preferred embodiment, said compound is selected from CoP-SQ (2D1), NiP CoP-SQ (2D2), or ZnP-SQ (2D3).

In another preferred embodiment, said catalyst of formula (I) is monometallic 2D-sheet polymer.

In yet another preferred embodiment, said catalyst of formula (I) is bimetallic 2D-sheet polymer.

In another embodiment, the present invention provides a one step process for the synthesis of novel squaraine linked metalloporphyrin based 2D-sheet polymer catalyst of formula (I) comprising heating the reaction mixture of metal porphyrin and acid compound in suitable solvent at temperature in the range of 120 to 125° C. for the period of 2.5 to 3 days.

In preferred embodiment, said metal porphyrin is selected from zinc porphyrin, cobalt porphyrin, nickel porphyrin, iron porphyrin, manganese porphyrin, molybdenum porphyrin or mixture thereof.

In another preferred embodiment, said metal porphyrin is selected from

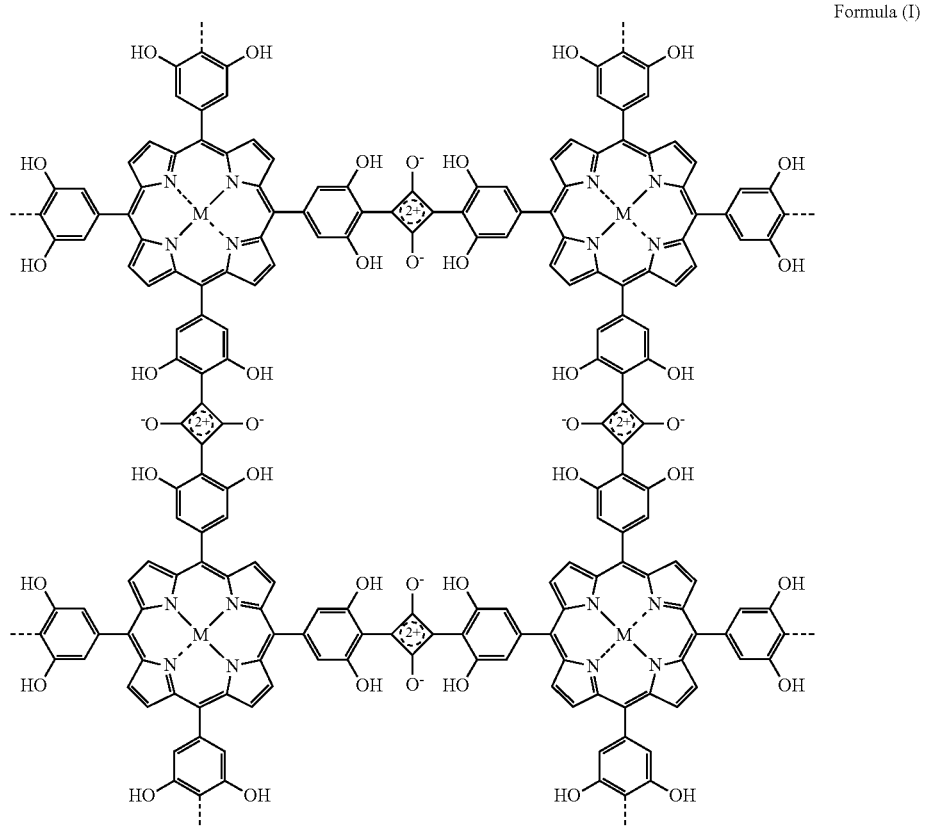

Formula (I)

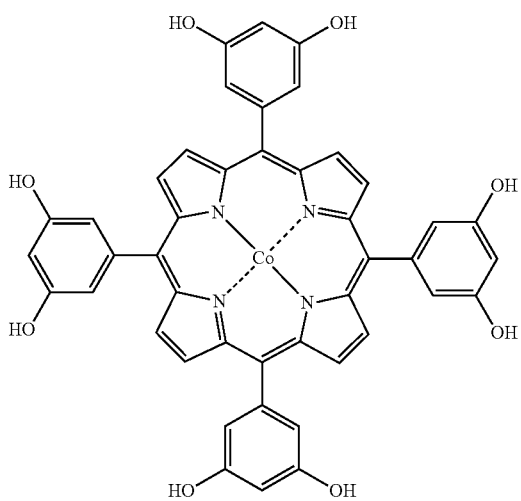

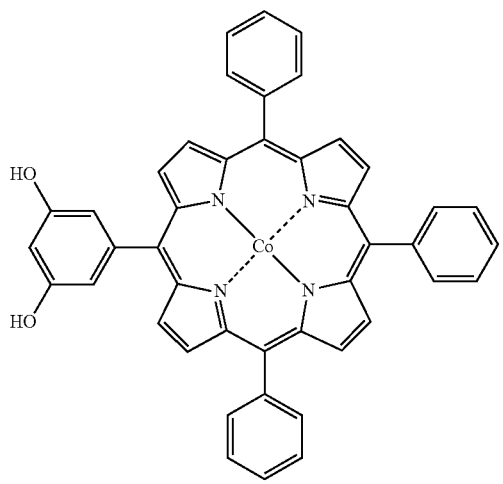

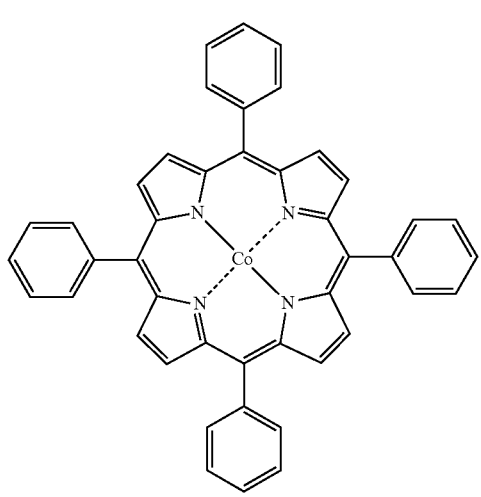

In yet another preferred embodiment, said acid compound is selected from squaric acid.

In still another preferred embodiment, said solvent is selected from n-butanol, toluene or mixture thereof.

In yet another embodiment, the present invention provides use of metalloporphyrin catalyst of formula (I) for generation of oxygen and hydrogen by splitting water photo catalytically and electro catalytically.

Abbreviations Used:

CoP: Co(II)-5,10,15,20-Tetrakis(3,5-dihydroxyphenyl) porphyrin

NiP: Ni (II)-5,10,15,20-Tetrakis(3,5-dihydroxyphenyl) porphyrin

HER: Hydrogen Evolution Reaction

P: porphyrin

SQ: squaraine

BRIEF DESCRIPTION OF THE DRAWINGS

FIG. 1: Characterization of the 2D-sheet catalyst. (A) Photograph of the polymer 2D1 suspension in MeOH. (B) Optical microscope image of the large area sheets of 2D1. (C) UV-Vis absorption of 2D1 in DMF and 1 in MeOH. Elemental mapping of 2D1. (D) Co—K, (E) N—K and (F) O—K. (G) TEM image of the 2D-sheets upon drop casting from MeOH suspension of 2D1 on carbon coated Cu grid and (H) a magnified TEM image showing the porous nature of the polymer.

FIG. 2: HER and OER performance of 2D1. (A) $H_2$ evolution performance of 2D1 (solely). (B) Optimization $H_2$ evolution with various sacrificial reagents. (C) Catalytic durability studies of $H_2$ evolution in the optimized condition (5 ml Triethanolamine, 5 mg catalyst 5 μl Pt cocatalyst). (D) $O_2$ evolution performance of 2D1 (solely). (E) Optimization $O_2$ evolution with various sacrificial reagents/Redox mediators. (F) Catalytic durability studies of $O_2$ evolution in the optimized condition (5 mg catalyst, 5 μl $AgNO_3$).

FIG. 3: (A) Photograph of polymer 2D2 films the suspension in MeOH. (B) Photograph of free standing polymer films of 2D2.

FIG. 4: HR-TEM images of TEM image of the 2D-sheets upon drop casting from MeOH suspension of 2D2 on carbon coated Cu grid.

FIG. 5: HER and OER performance of 2D2. (A) $H_2$ evolution performance of 2D2 (5 ml Triethanolamine, 5 mg catalyst) $O_2$ evolution in the optimized condition of 2D2 (5 mg catalyst, 5 μl $AgNO_3$).

FIG. 6: Solid State UV Absorption Spectrum of 2D1 & 2D2.

FIG. 7: Electrocatalytic water splitting (OER) performance of 2D1. (A) Optimization of vulcan carbon for the catalytic performance of pristine catalyst (B) Catalytic durability studies of $O_2$ evolution in the optimized condition pristine catalyst, vulcan carbon (1:1) chronoamperometry stability more than 12 hr.

DETAILED DESCRIPTION OF THE INVENTION

The invention will now be described in detail in connection with certain preferred and optional embodiments, so that various aspects thereof may be more fully understood and appreciated.

In an embodiment, the present invention provides a novel squaraine linked metalloporphyrin based 2D-sheet polymer catalyst with basic unit of formula (I);

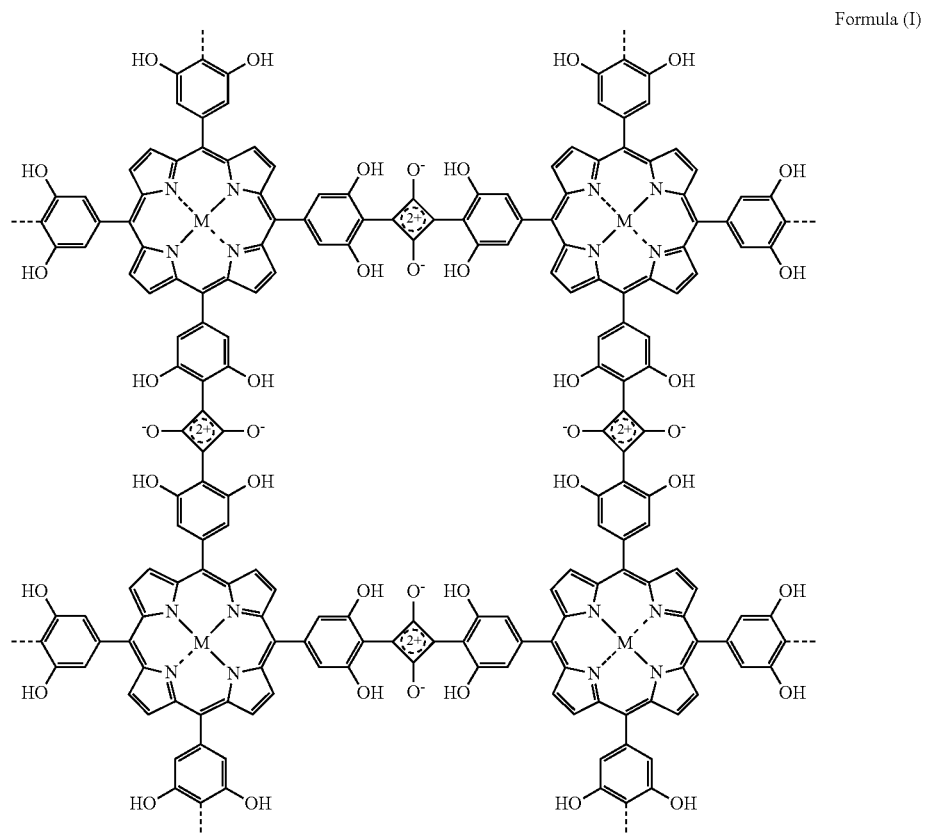

Formula (I)

wherein;

M is selected from cobalt, nickel, zinc, copper, iron, manganese, molybdenum or mixture thereof.

In preferred embodiment, said compound is selected from
a) CoP-DQ (2D1)
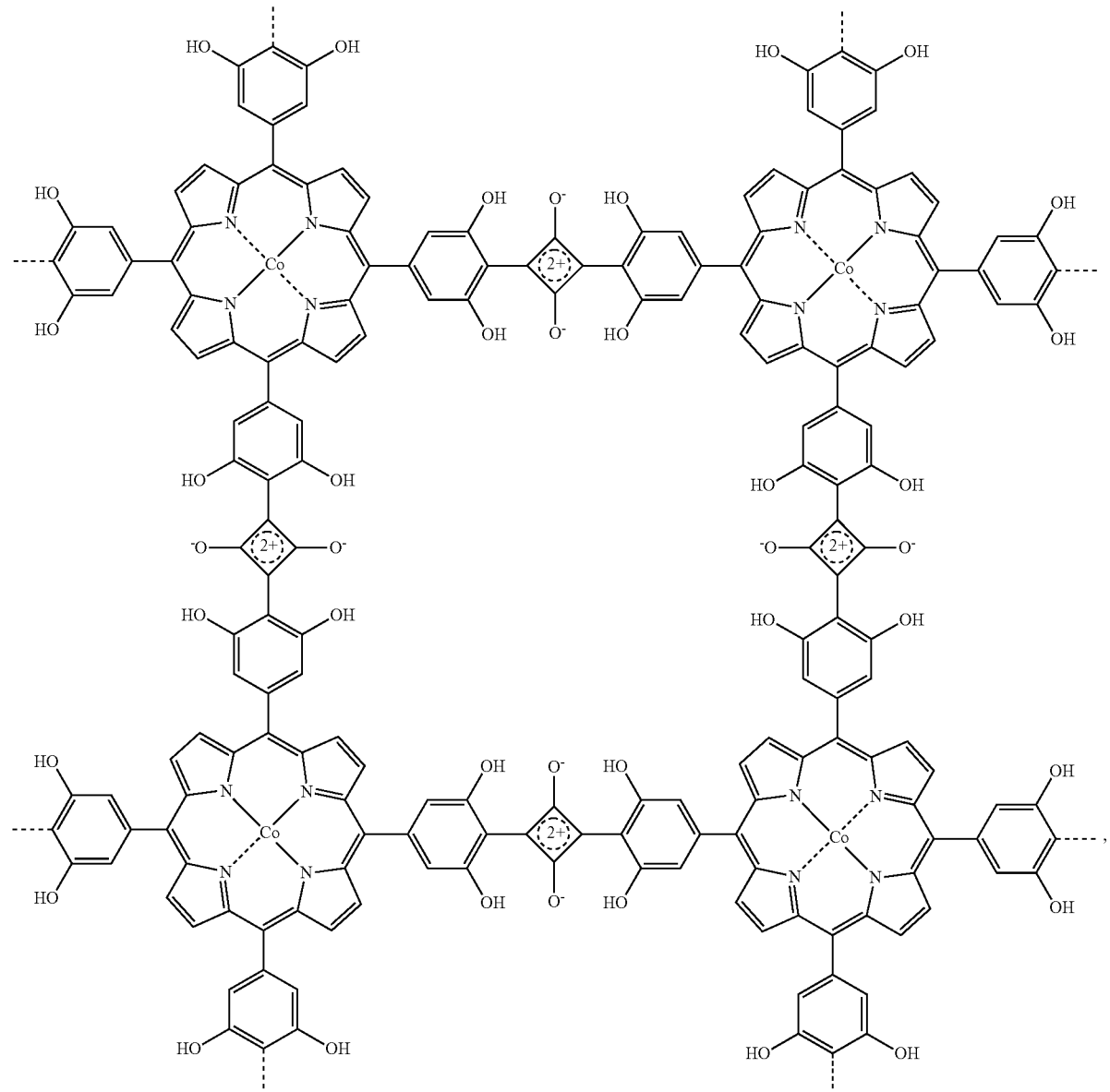

-continued
b) NiP CoP-SQ (2D2)
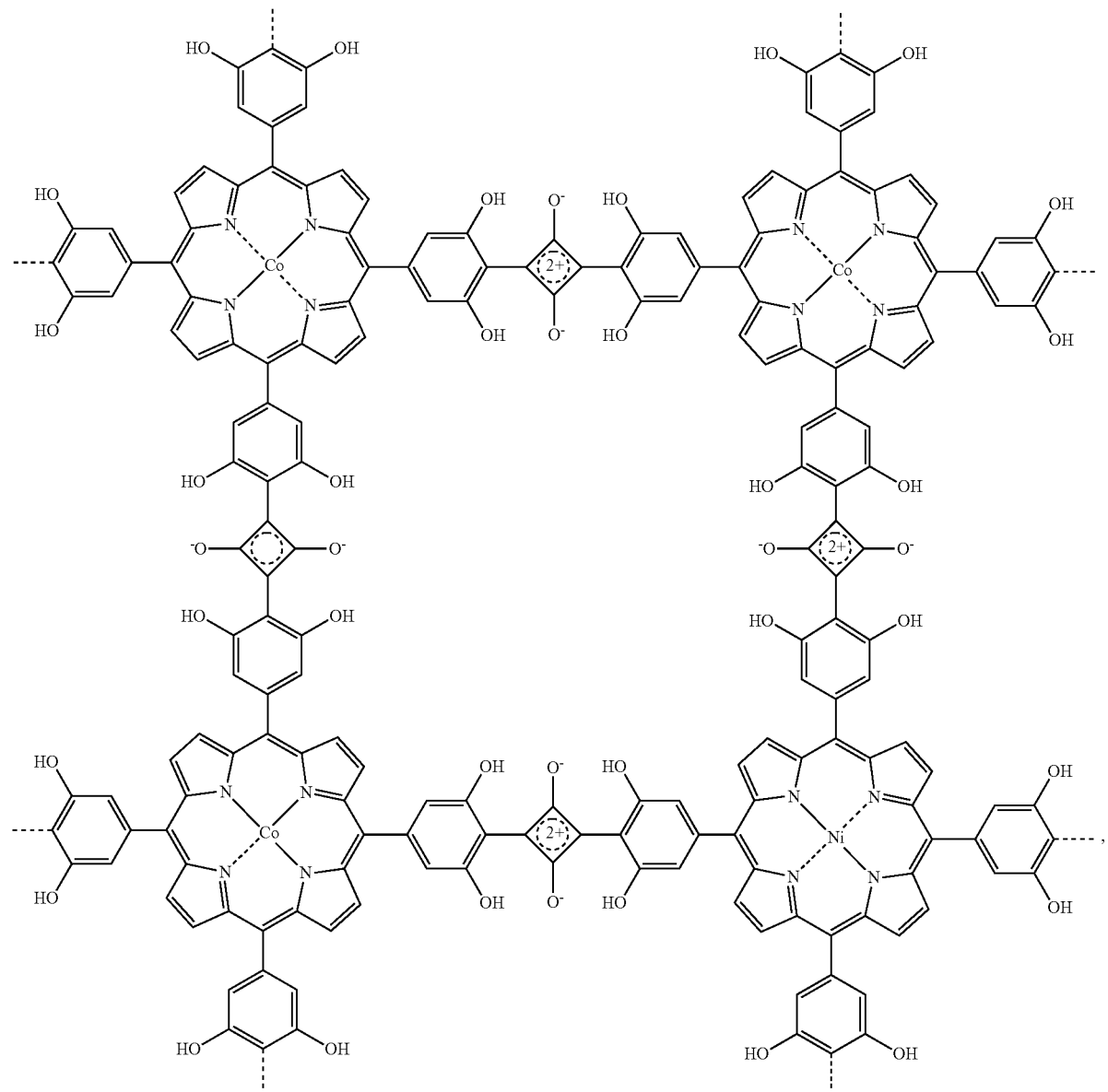

c) ZnP-SQ(2D3)
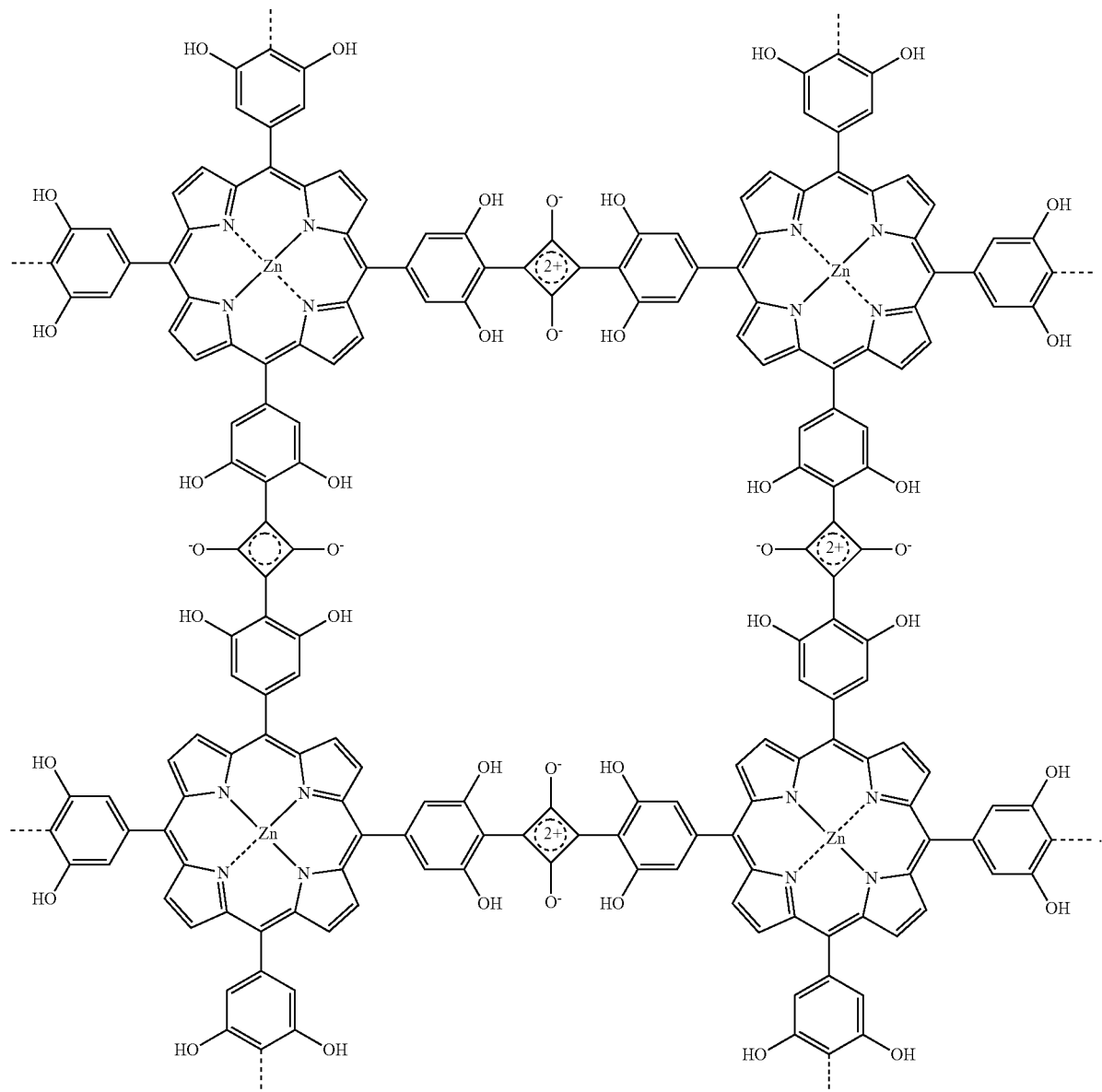

In another preferred embodiment, said catalyst of formula (I) is monometallic 2D-sheet polymer.

In yet another preferred embodiment, said catalyst of formula (I) is bimetallic 2D-sheet polymer.

In another embodiment, the present invention provides a one step process for the synthesis of novel squaraine linked metalloporphyrin based 2D-sheet polymer catalyst of formula (I) comprising heating the reaction mixture of metal porphyrin and acid compound in suitable solvent at temperature in the range of 120 to 125° C. for the period of 2.5 to 3 days.

In preferred embodiment, said metal porphyrin is selected from zinc porphyrin, cobalt porphyrin, nickel porphyrin, iron porphyrin, manganese porphyrin, molybdenum porphyrin or mixture thereof.

In another preferred embodiment, said metal porphyrin is selected from

2
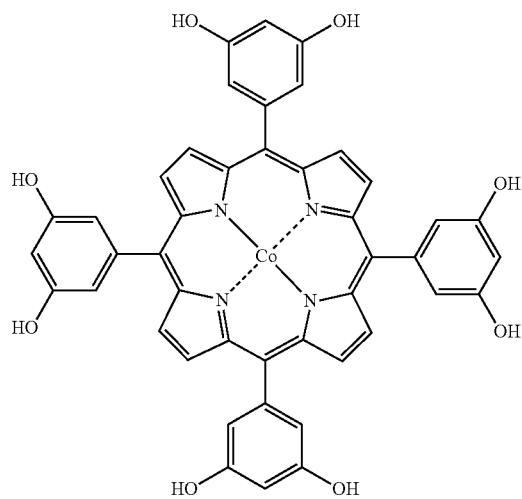

3
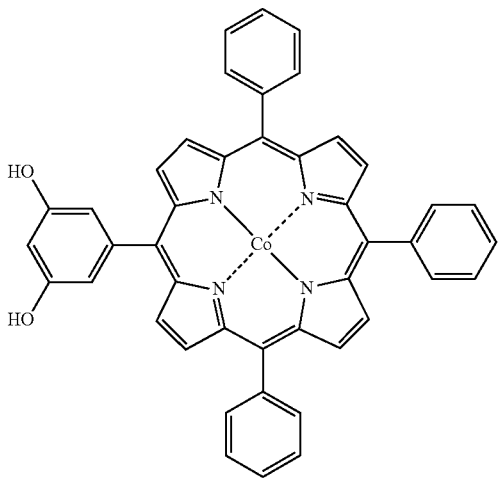

4
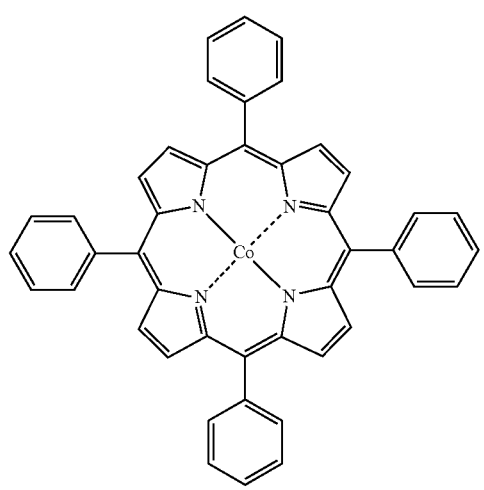

In yet another preferred embodiment, said acid compound is squaric acid.

In still another preferred embodiment, said solvent is selected from n-butanol, toluene or mixture thereof.

The one step process for the synthesis of novel squaraine linked metalloporphyrin based 2D-sheet polymer catalyst of formula (I) is as shown in scheme 1 below:

Scheme: 1

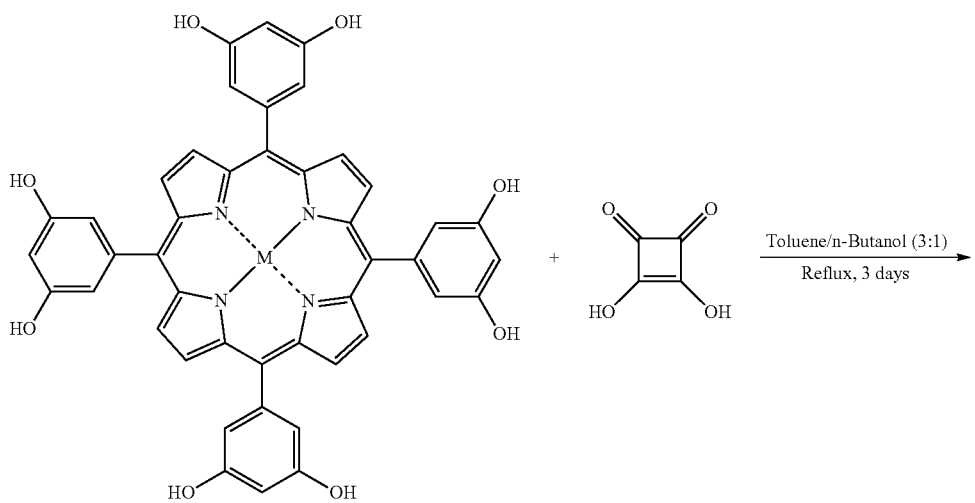

-continued

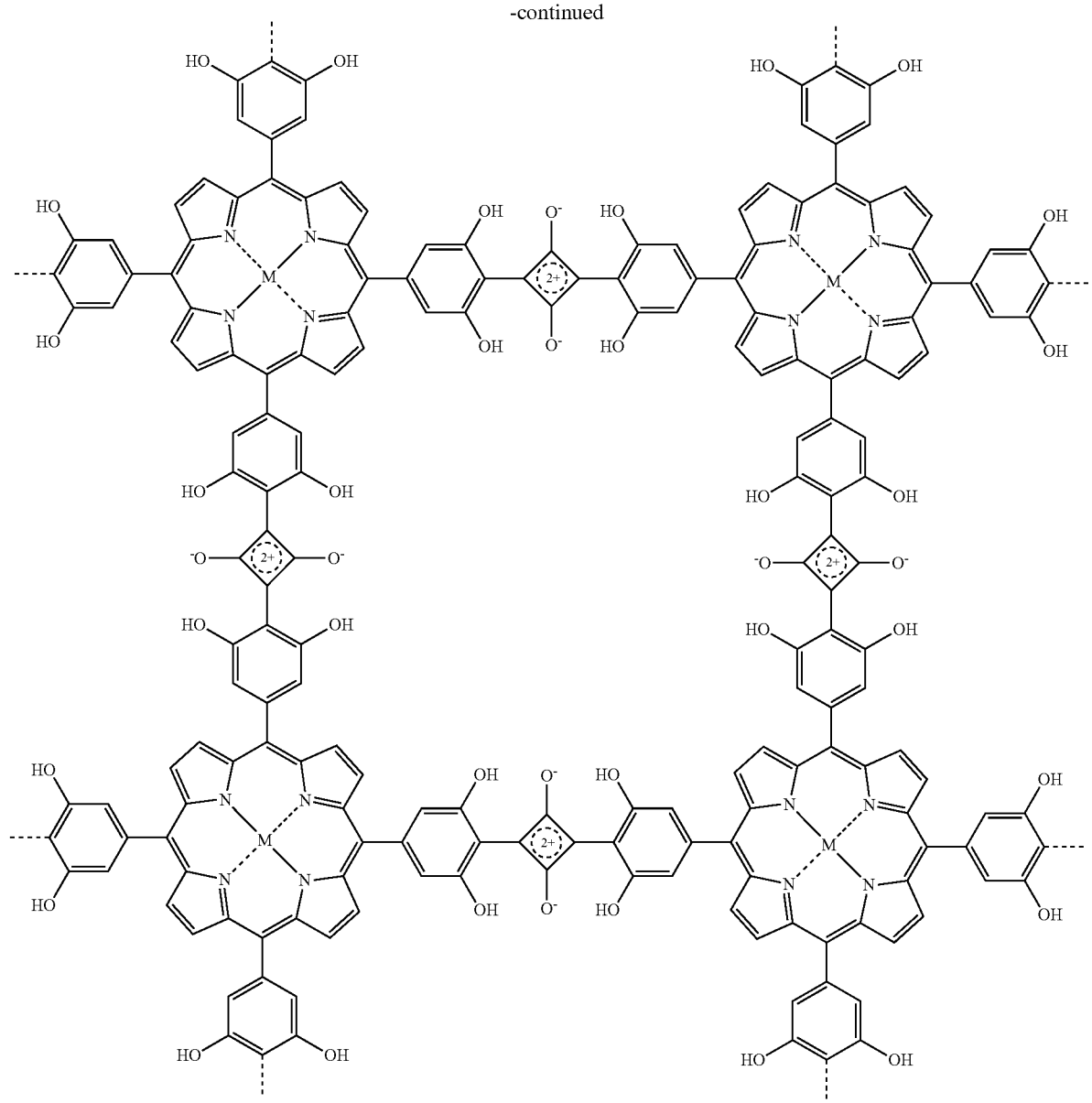

2D1: M = Co
2D2: M = Co/Ni (1:1)
2D3: M = Zn

In yet another embodiment, the present invention provides use of metalloporphyrin catalyst of formula (I) for generation of oxygen and hydrogen by splitting water photo catalytically and electro catalytically.

In preferred embodiment, the present invention provides an octahydroxy decorated metalloporphyrin based two dimensional (2D) sheet polymers of formula (I) for photo and electrocatalytic water splitting leading to both hydrogen and oxygen evolution without much assistance of cocatalysts/redox mediator.

The presence of many hydroxyl groups at the close proximity of the metal centre is one of the key aspects of this catalyst. The intriguing thought of having alternate polar (squarine) and apolar (metal porphyrin) regions of the framework is distinctly different from the conventional hydrophobic 2D-polymers. Hence, the polar environment around the metal centre will enhance the local concentration of water molecules available for HER and OER. The high-surface area of the catalyst brings porosity, thereby improves the catalytic activity as well as long-term stability.

The FIG. 1 depicts characterization of the 2D-sheet catalyst. (A) Photograph of the polymer 2D1 suspension in MeOH. (B) Optical microscope image of the large area sheets of 2D1. (C) UV-Vis absorption of 2D1 in DMF and 1 in MeOH. Elemental mapping of 2D1 for (D) Co—K, (E) N—K, and (F) O—K. (G) TEM image of the 2D-sheets upon drop casting from MeOH suspension of 2D1 on carbon coated Cu grid and (H) a magnified TEM image showing the porous nature of the polymer.

The FIG. 2 shows HER and OER performance of 2D1. (A) $H_2$ evolution performance of 2D1 (solely). (B) Optimization $H_2$ evolution with various sacrificial reagents. (C)

Catalytic durability studies of $H_2$ evolution in the optimized condition (5 ml Triethanolamine, 5 mg catalyst 5 μl Pt co catalyst). (D) $O_2$ evolution performance of 2D1 (solely). (E) Optimization $O_2$ evolution with various sacrificial reagents/ Redox mediators. (F) Catalytic durability studies of $O_2$ evolution in the optimized condition (5 mg catalyst, 5 μl $AgNO_3$). The FIG. 5 shows HER and OER performance of 2D2. (A) $H_2$ evolution performance of 2D2 (5 ml Triethanolamine, 5 mg catalyst) $O_2$ evolution in the optimized condition of 2D2 (5 mg catalyst, 5 μl $AgNO_3$). In FIGS. 2 and 5 for photo hydrogen evolution (HER), methanol, TEA and so on used as sacrificial agents, for $O_2$ (OER) evolution, iodides, $AgNO_3$ added to increase efficiency. The cycles are repeated over 120 days and efficiency is found to be maintained for both $H_2$ and $O_2$.

The FIG. 3(A) depicts photograph of polymer 2D2 films the suspension in MeOH and FIG. 3 (B) Photograph of free standing polymer films of 2D2.

The FIG. 4 depicts HR-TEM images of TEM image of the 2D-sheets upon drop casting from MeOH suspension of 2D2 on carbon coated Cu grid.

The FIG. 6 depicts solid State UV Absorption Spectrum of 2D1 & 2D2.

The FIG. 7 shows Electrocatalytic water splitting (OER) performance of 2D1. (A) Optimization of vulcan carbon for the catalytic performance of pristine catalyst (B) Catalytic durability studies of $O_2$ evolution in the optimized condition pristine catalyst, vulcan carbon (1:1) chronoamperometry stability more than 12 hr. From FIG. 7, the electrocatalytic water splitting with the evolution of oxygen is observed at lower over potential. Conducting vulcan carbon is used as additive and improved performance noted, along with stability up to 12 hours, performance does not change over 100 days.

The following examples, which include preferred embodiments, will serve to illustrate the practice of this invention, it being understood that the particulars shown are by way of example and for purpose of illustrative discussion of preferred embodiments of the invention.

EXAMPLES 5,10,15,20-Tetrakis(3,5-dimethoxyphenyl)porphyrin, 5,10,15,20-Tetrakis(3,5-dihydroxyphenyl)porphyrin(XX) prepared and characterized according to the literature report.

Example 1: Preparation of Zinc Porphyrin 5,10,15,20-Tetrakis(3,5-dihydroxyphenyl)porphyrin (100 mg, 134.64 μmol) and zinc acetate dihydrate (123.5 mg, 673.19 μmol) were dissolved in chloroform (5 mL) and methanol (10 mL). The solution was stirred at room temperature under nitrogen for 12 h; the mixture was then brought to dryness on a rotary evaporator then dried mass was dissolved in Ethyl acetate (30 mL) and washed with water (100 mL). The organic layer was dried over Sodium sulfate ($Na_2SO_4$) and then evaporated to constant weight. The residue dried at room temperature for several hours in vacuum, to give a dark purple crystalline product with quantitative yield. LC-HRMS: m/z 805.1255 (MH+); [$C_{44}H_{29}N_4O_8Zn$].

Example 2: Preparation of Cobalt Porphyrin 5,10,15,20-Tetrakis(3,5-dihydroxyphenyl)porphyrin (100 mg, 134.64 μmol), 2,6-dimethylpyridine (31 μL, 269.28 μmol), and anhydrous cobalt(II) chloride (70 mg, 538.55 μmol) were dissolved in dry THF(20 ml) and heated to reflux under Argon. The reaction was complete after 2 h. The mixture was then brought to dryness on a rotary evaporator, extracted with ethyl acetate and the resulting solution chromatographed on a dry silica gel column using chloroform-methanol (20:2 v/v) as the eluant. The eluate was reduced to small volume on a rotary evaporator and the residue dried at room temperature for several hours in Vacuum, to give a dark purple crystalline product (XY) further purified by recrystallization from distilled methanol and chloroform mixture. (105 mg, 97.5%); $R_f$=0.50 (chloroform-Methanol, 20:2 v/v). LC-HRMS: m/z 799.1217 (MH+); $C_{44}H_{29}CoN_4O_8$.

Example 3: Preparation of Nickel Porphyrin 5,10,15,20-Tetrakis(3,5-dihydroxyphenyl)porphyrin (100 mg, 134.64 μmol), 2,6-dimethylpyridine (31 μL, 269.28 μmol), and nickel (II) acetate tetrahydrate (120 mg, 673 μmol) were dissolved in dry THF (10 ml) dimethyl formamide (20 mL). The solution was stirred at 100° C. under nitrogen for 24 h. μmol) were dissolved in dry THF (20 ml) and heated to reflux under Argon. The mixture was then brought to dryness on a rotary evaporator, extracted with ethyl acetate then washed with water (3×30 mL). The organic layer was dried over $Na_2SO_4$ and evaporated to dryness on a rotary evaporator and the residue dried at room temperature for several hours in vacuum, to give a dark purple crystalline product with quantitative yield (Ni (II)-5, 10,15,20-Tetrakis(3,5-dihydroxyphenyl)porphyrin) further purified by recrystallization from distilled methanol and chloroform mixture. LC-HRMS: m/z 799.1318 (MH+); $C_{44}H_{29}N_4NiO_8$.

Example 4: CoP-SQ Polymer Synthesis (2D1)

The mixture of CoP (XY) (25 mg, 31.26 μmol) and squaric acid (7.84 mg, 68.78 μmol) in n-butanol/toluene (4 mL, ⅓ in vol.) was degassed in Pyrex tube (10 mL) by three freeze-pump-thaw cycles. The tube was vacuum-sealed off and heated at 125° C. for 3 days. The polymer precipitated out from solution as 2D sheets (FIG. 1). The precipitate was collected by centrifugation, washed with distilled methanol for 10 times and dried at 100° C. under vacuum for 5 h, to give CoP-SQ 2D polymer as a dark brownish purple fluffy material in 30 mg (best) isolation yield. 10 mg and 15 mg CoP used batches forming thin films while 20 mg and 25 mg CoP used batches product was precipitating from the solution as a dark brownish purple fluffy material.

Example 5: NiP, CoP-SQ 2D Polymer Synthesis (2D2)

The mixture of CoP (XY) (10 mg, 12.5 μmol), NiP (XZ) (10 mg, 12.5 μmol) and squaric acid (6 mg, 52.5 μmol) in n-butanol/toluene (4 mL, ⅓ in vol.) was degassed in Pyrex tube (10 mL) by three freeze-pump-thaw cycles. The tube was vacuum-sealed off and heated at 125° C. for 3 days. The polymer precipitated out from solution as 2D sheets (FIG. 3) The precipitate was collected by centrifugation, washed with distilled methanol about 10 times and dried at 100° C. under vacuum for 5 h, to give CoP-SQ 2D(2D2) polymer as a dark brownish purple fluffy material in 22 mg (best) isolation yield.

Example 6: ZnP-SQ Polymer Synthesis (2D3)

Similar procedure of 2D1 adopted for the synthesis of 2D3 also.

Example 7: CoP-SQ Dimer (1)

Squaric acid was added to a solution of 2 equiv of the corresponding dihydroxyporphyrin (3) in toluene/1-butanol (3:1.) was degassed in Pyrex tube (10 mL) by three freeze-pump-thaw cycles. The tube was vacuum-sealed off and heated at 125° C. for one day. After the dark purple reaction mixture was cooled to room temperature, the mixture was then brought to dryness on a rotary evaporator, extracted with ethyl acetate then washed with water (3×30 mL). The organic layer was dried over $Na_2SO_4$ and evaporated to dryness on a rotary evaporator and the residue dried at room temperature for several hours in vacuum, to give a dark purple crystalline product with quantitative yield. Characterized with Maldi-TOF (α-Cyano-4-hydroxycinnamic acid matrix) m/z 1486.2318 (MH+), UV spectroscopy.

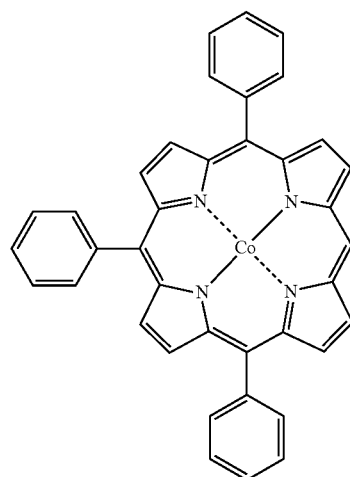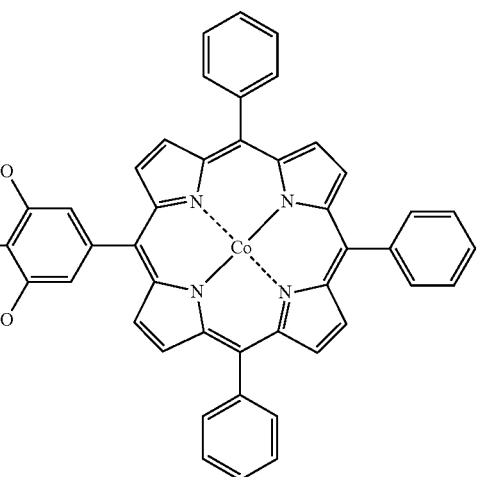

1

Example 8: Electro Catalytic Water Splitting Using Compound of Formula (I)

A. Functionalization of Vulcan Carbon:

About 1 g of Vulcan carbon was refluxed with 200 mL of 30% $H_2O_2$ at 60° C. for 8 h in an oil bath. The material was allowed to cool and then filtered. The wet cake thus obtained was dried at 50° C. for 5 h in a vacuum oven. The material as obtained was directly used to make the catalyst slurry for the electrochemical analysis by mixing with the catalyst.

B. Oxygen Evolution Reaction (OER)

The oxygen evolution reaction (OER) of the material was analysed using the Bio-Logic (SP-300) instrument in a three electrode set-up. By following procedure, catalyst ink for the analysis has been made. 2.5 mg of the catalyst and 2.5 mg of functionalized Vulcan carbon were physically mixed and dispersed well with the mixture of 3:1 DI water-isopropyl alcohol and 40 μL of 5 wt. % Nafion solution (Dupont) by 1 h bath sonication. About 5 μL of the catalyst ink was coated on the glassy carbon working electrode (0.0706 $cm^2$) and kept for drying. Hg/HgO was used as the reference electrode and graphite rod was used as the counter electrode. All the analyses were carried out in the $N_2$ saturated 1M KOH solution. The potentials were converted into RHE by calibrating the Hg/HgO reference electrode in $H_2$ saturated 1M KOH solution by running the linear sweep voltammetry at a scan rate of 1 mV $sec^{-1}$, the conversion factor was 0.917 V. The electro catalytic water splitting with the evolution of oxygen is observed at lower over potential. Conducting vulcan carbon is used as additive and improved performance noted, along with stability up to 12 hours, performance does not change over 100 days.

Example 9: Electro Catalytic Water Splitting Using 2D1

A. Functionalization of Vulcan Carbon

About 1 g of Vulcan carbon was refluxed with 200 mL of 30% $H_2O_2$ at 60° C. for 8 h in an oil bath. The material was allowed to cool and then filtered. The wet cake thus obtained was dried at 50° C. for 5 h in a vacuum oven. The material as obtained was directly used to make the catalyst slurry for the electrochemical analysis by mixing with the catalyst.

B. Oxygen Evolution Reaction (OER)

The oxygen evolution reaction (OER) of the material was analysed using the Bio-Logic (SP-300) instrument in a three electrode set-up. By following procedure, catalyst ink for the analysis has been made. 2.5 mg of the CoP-SQ Polymer (2D1) as a catalyst and 2.5 mg of functionalized Vulcan carbon were physically mixed and dispersed well with the mixture of 3:1 DI water-isopropyl alcohol and 40 μL of 5 wt. % Nafion solution (Dupont) by 1 h bath sonication. About 5 μL of the catalyst ink was coated on the glassy carbon working electrode (0.0706 $cm^2$) and kept for drying. Hg/HgO was used as the reference electrode and graphite rod was used as the counter electrode. All the analyses were carried out in the $N_2$ saturated 1M KOH solution. The potentials were converted into RHE by calibrating the Hg/HgO reference electrode in $H_2$ saturated 1M KOH solution by running the linear sweep voltammetry at a scan rate of 1 mV $sec^{-1}$, the conversion factor was 0.917 V.

Advantages of Invention

1. The real struggle of releasing $H_2$ and $O_2$ from water is accounted by a sensible design and thereby impressive performance from 2D sheet catalyst.
2. The presence of many hydroxyl groups at the close proximity of the metal centre is one of the key aspects of this catalyst.
3. The high-surface area of the catalyst brings porosity, thereby improves the catalytic activity as well as long-term stability.
4. Photo and electrocatalytic $H_2$ and $O_2$ evolution achieved by a single durable catalyst system.

We claim:

1. A novel squaraine linked metalloporphyrin based 2D-sheet polymer compound with basic unit of formula (I);

wherein;

M is selected from the group consisting of cobalt, nickel, zinc, copper, iron, manganese, molybdenum or a mixture thereof.

2. The compound as claimed in claim 1, wherein said compound of formula (I) is monometallic 2D-sheet polymer.

3. The compound as claimed in claim 1, wherein said compound of formula (I) is bimetallic 2D-sheet polymer.

4. The compound as claimed in claim 2, wherein said compound is selected from the group consisting of:

Formula (I)

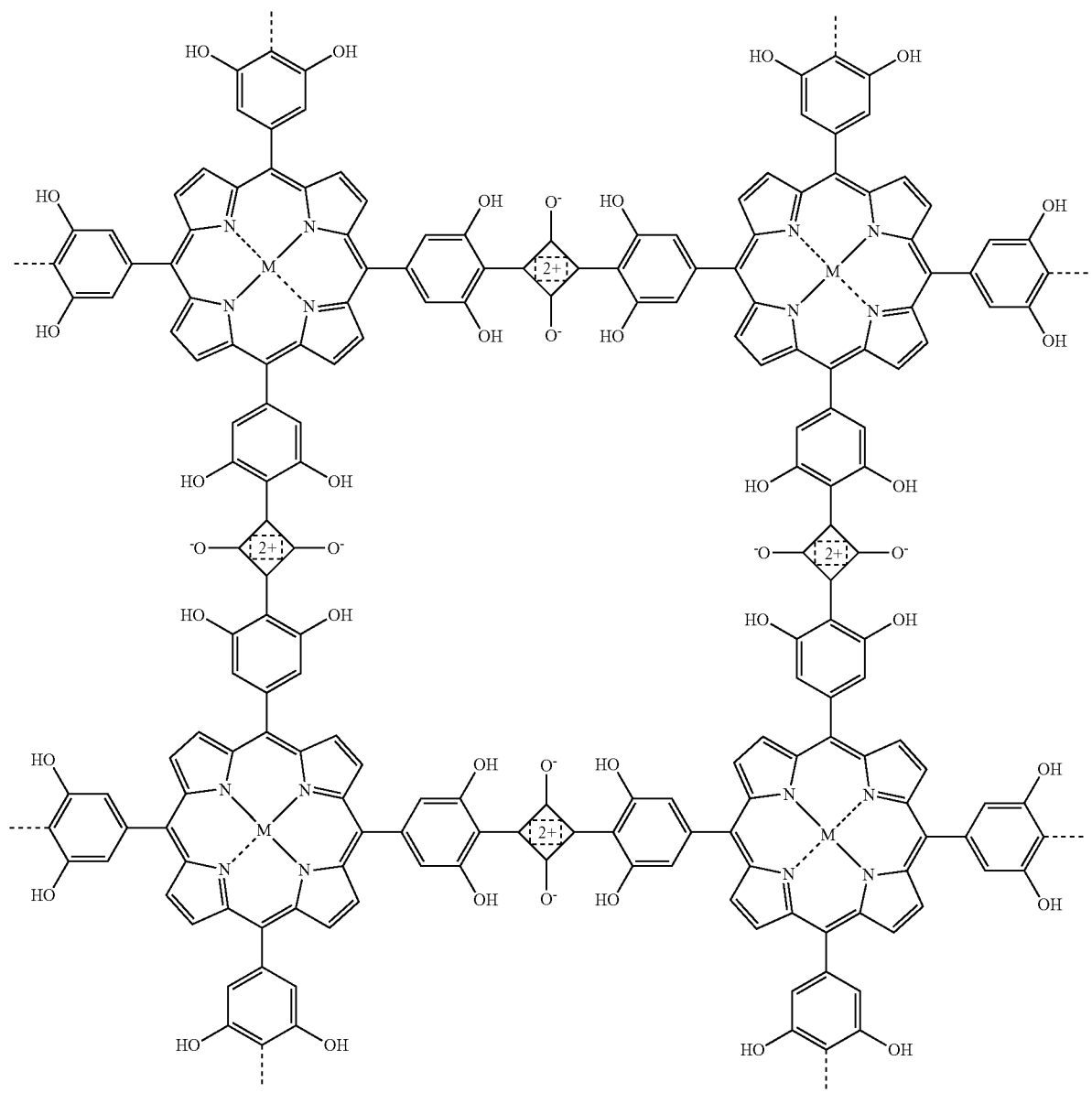

a) CoP-SQ (2D1),
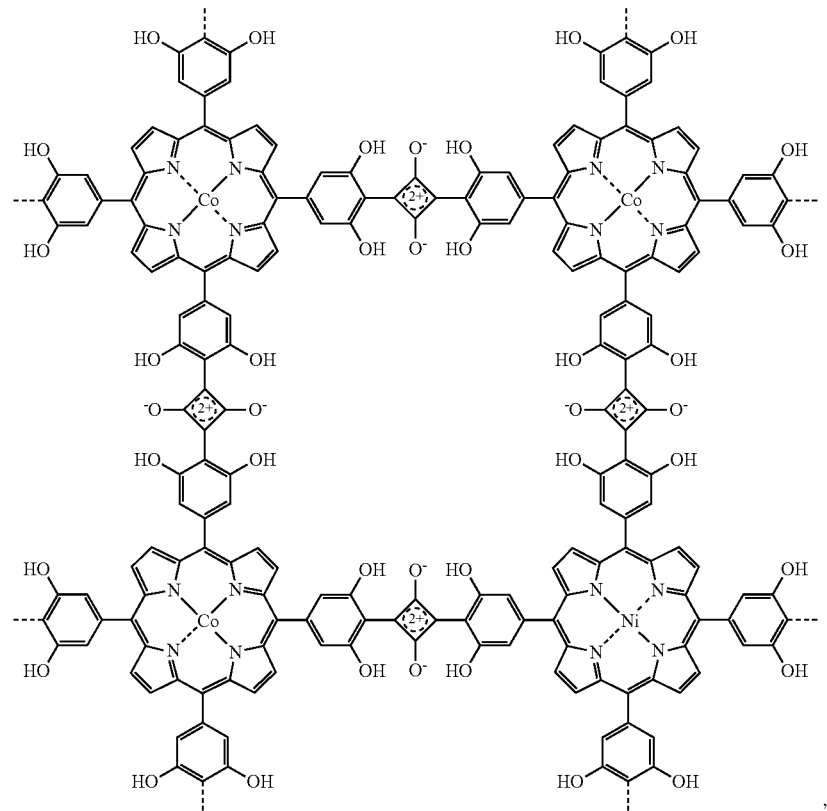
and b) ZnP-SQ (2D3)

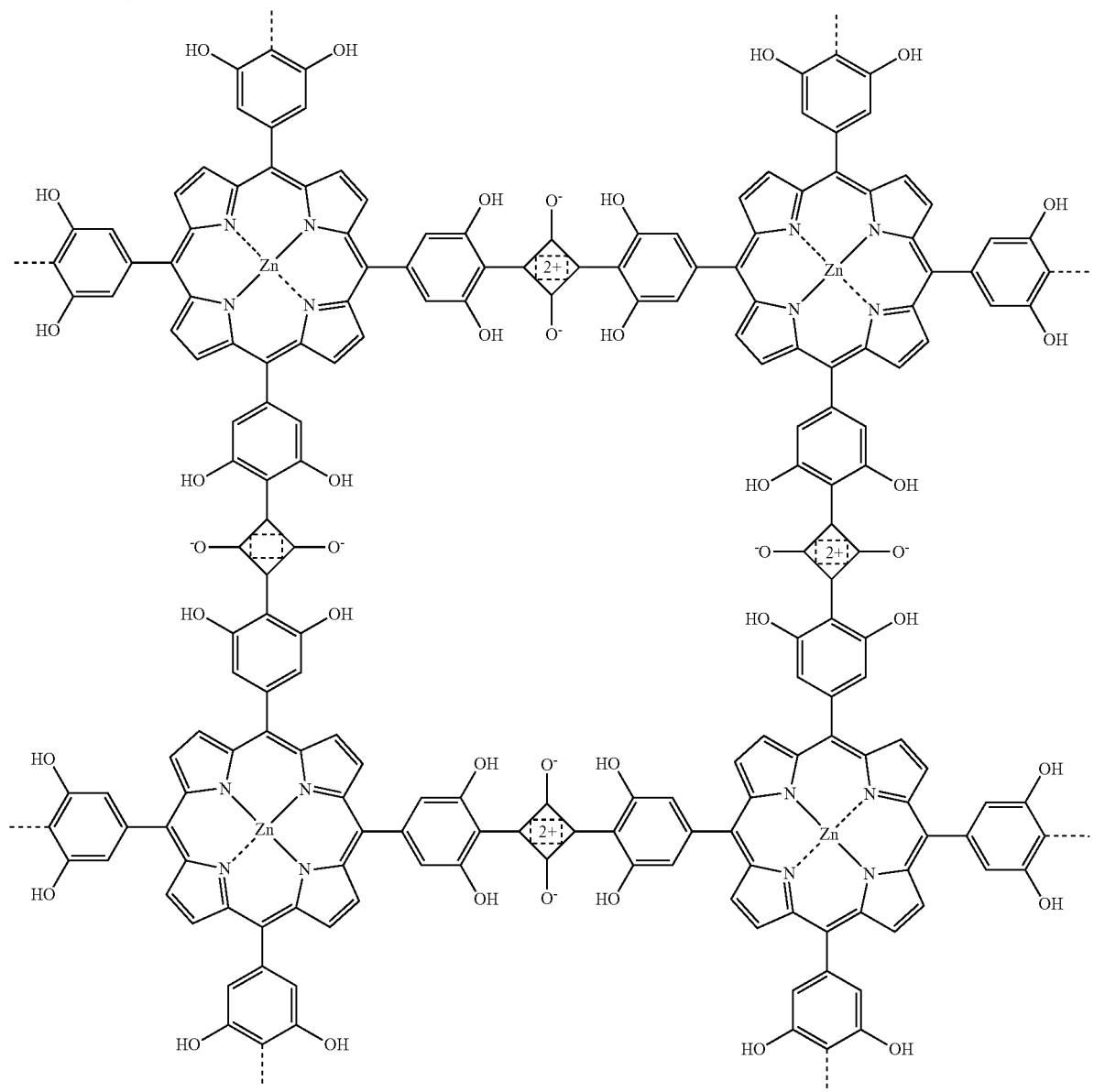

5. The compound as claimed in claim 1, wherein said compound of formula (I) is used for generation of oxygen and hydrogen by splitting water photo catalytically and electro catalytically.

6. A one step process for the synthesis of novel squaraine linked metalloporphyrin based 2D-sheet polymer compound with basic unit of formula (I) as claimed in claim 1, wherein said process comprises heating a reaction mixture of metal porphyrin and an acid compound in suitable solvent at a temperature in the range of 120 to 125° C. for a period of 2.5 to 3 days;

wherein said acid compound is squaric acid.

7. The process as claimed in claim 6, wherein said metal porphyrin is selected from the group consisting of zinc porphyrin, cobalt porphyrin, nickel porphyrin, iron porphyrin, manganese porphyrin, molybdenum porphyrin or mixture thereof.

8. The process as claimed in claim 6, wherein said metal porphyrin is selected from the group consisting of

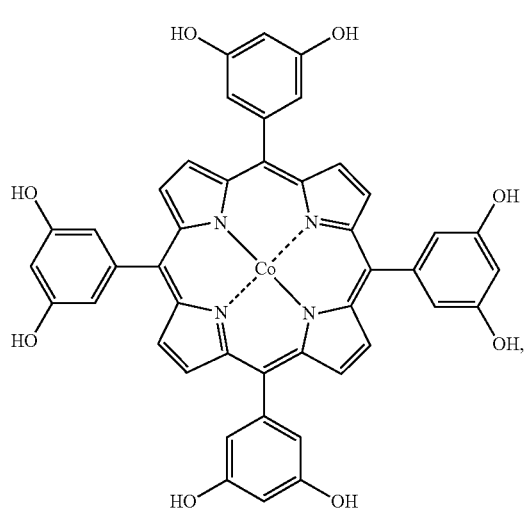

3
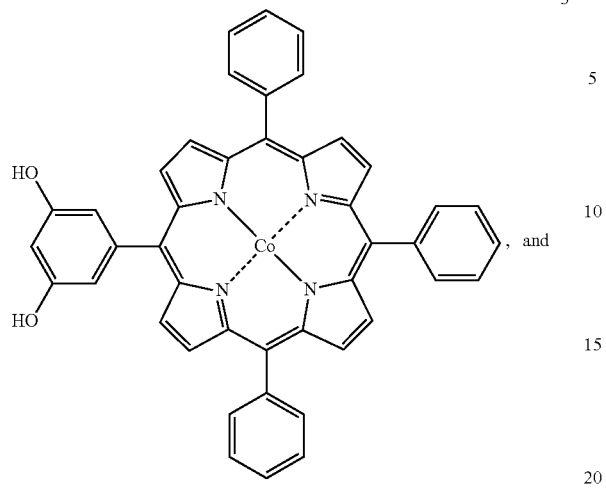
, and
4
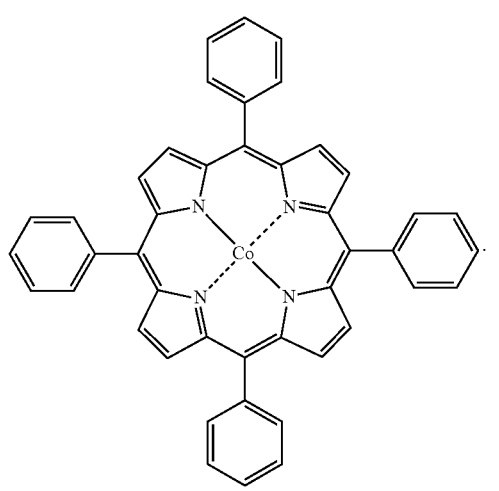
.
9. The process as claimed in claim 6, wherein said solvent is selected from the group consisting of n-butanol, toluene or mixture thereof.

10. The compound as claimed in claim 3, wherein said compound is NIP CoP-SQ (2D2):
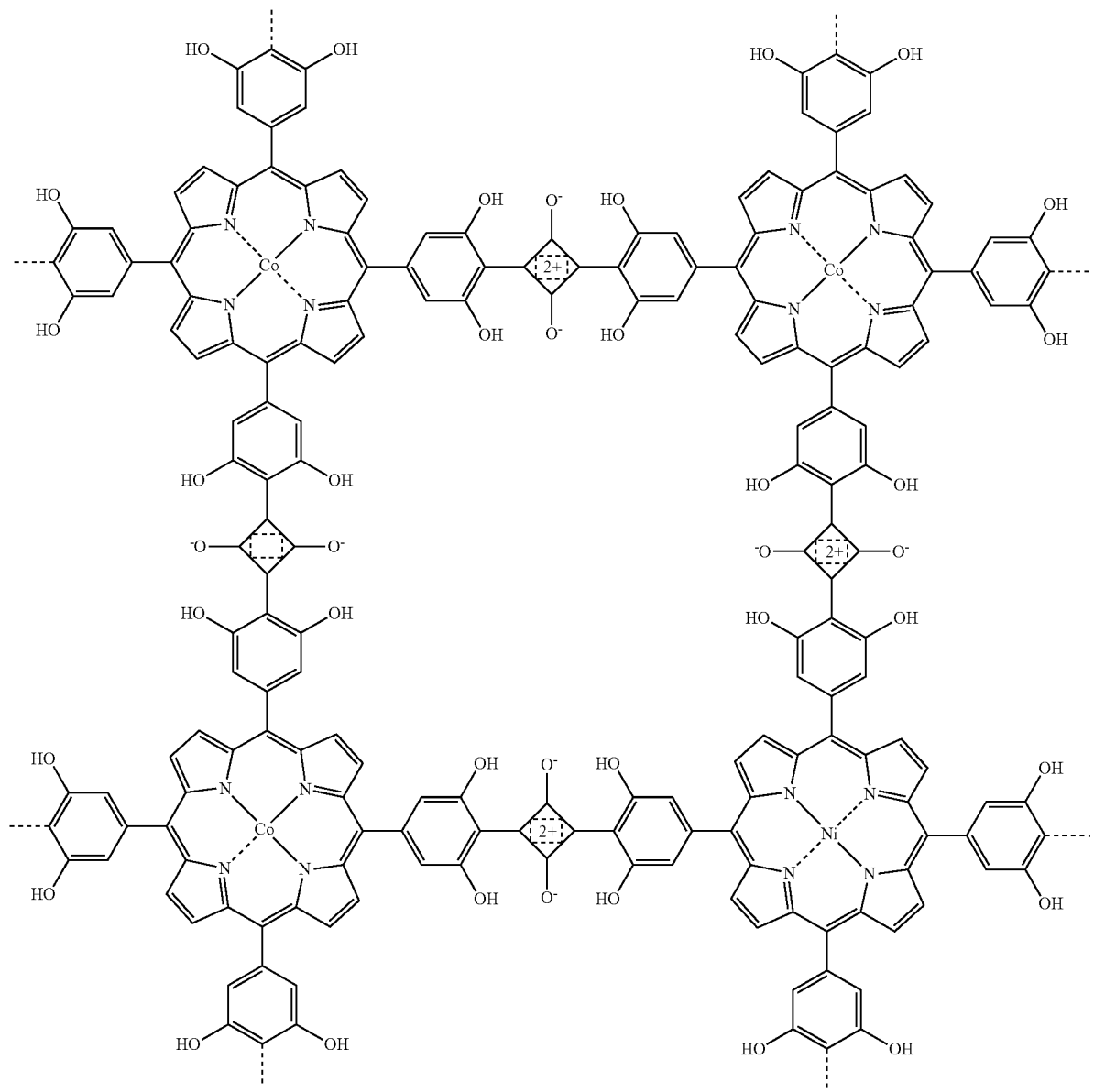
* * * * *